United States Patent
Tanji et al.

(10) Patent No.: US 9,095,513 B2
(45) Date of Patent: Aug. 4, 2015

(54) ENTERIC COATED GRANULE AND METHOD FOR PREPARING THE SAME

(75) Inventors: Mutsunori Tanji, Fukushima (JP); Tadashi Matsui, Fukushima (JP); Shuichiro Yuasa, Fukushima (JP); Yuichi Nishiyama, Joetsu (JP); Yuichi Ito, Tokyo (JP); Ikuo Fukui, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 1670 days.

(21) Appl. No.: 11/764,084

(22) Filed: Jun. 15, 2007

(65) Prior Publication Data

US 2007/0292509 A1    Dec. 20, 2007

(30) Foreign Application Priority Data

Jun. 16, 2006  (JP) ................................. 2006-167814

(51) Int. Cl.
*A61K 9/16*   (2006.01)
*A61K 9/50*   (2006.01)

(52) U.S. Cl.
CPC ............. *A61K 9/1688* (2013.01); *A61K 9/1652* (2013.01); *A61K 9/5026* (2013.01); *A61K 9/5042* (2013.01); *A61K 9/5073* (2013.01)

(58) Field of Classification Search
CPC ..... A61K 9/1652; A61K 9/1688; A61K 9/50; A61K 9/5005; A61K 9/5026; A61K 9/5073
See application file for complete search history.

(56) References Cited

U.S. PATENT DOCUMENTS

| | | | |
|---|---|---|---|
| 5,540,945 A * | 7/1996 | Ikushima | 424/490 |
| 5,656,290 A | 8/1997 | Kelm et al. | |
| 5,843,479 A | 12/1998 | Kelm et al. | |
| 6,893,662 B2 * | 5/2005 | Dittmar et al. | 424/472 |
| 2002/0098235 A1 | 7/2002 | Dittmar et al. | |
| 2004/0028737 A1* | 2/2004 | Deshpande et al. | 424/474 |
| 2004/0067257 A1* | 4/2004 | Bateman et al. | 424/471 |
| 2005/0169996 A1 | 8/2005 | Dittmar et al. | |
| 2005/0181053 A1 | 8/2005 | Dittmar et al. | |
| 2006/0159760 A1* | 7/2006 | Yoneyama et al. | 424/472 |
| 2007/0287719 A1* | 12/2007 | Boyden et al. | 514/265.1 |

FOREIGN PATENT DOCUMENTS

| | | |
|---|---|---|
| JP | 8-109126 A | 4/1996 |
| WO | WO 96/36321 | 11/1996 |
| WO | WO 2004080439 A1 * | 9/2004 |

OTHER PUBLICATIONS

Fukasawa, Miyuki; Obara, Sakae; Molecular Weight Determination of Hypromellose Acetate Succinate (HPMCAS) Using Size Exclusion Chromatography with a Multi-Angle Laser Light Scattering Detector; Pharmaceutical Society of Japan; Chemical and Pharmaceutical Bulletin, vol. 52, No. 11, pp. 1391-1393.*
Shin-Etsu AQOAT™ product literature, Shin-Etsu Chemical Co., Ltd. pp. 1-20.*
Nagai, Tsuneji; Obara, Sakae; Kokubo, Hiroyasu; Hoshi, Noboru; "Application of HPMC and HPMCAS to Aqueous Film Coating of Pharmaceutical Dosage Forms," 1997, M. Dekker New York; Aqueous Polymeric Coatings for Pharmaceutical Dosage forms, McInty, J.W. ed., pp. 177-226.*
Leopold, Claudia S.; "A Practical Approach in the Design of Colon-specific Drug Delivery Systems," 2001, Wiley-VCH Verlag GmbH; Drug Targeting Organ-Specific Strategies, G. Molema & D.K. Meijer eds.; Chapter 6, pp. 157-170.*
Eudragit™ product literature retrieved from <eudragit.evonik.com/product/en/downloads/eudragit-brochures/pages/default.aspx> on Apr. 16, 2010.*
Eudragit™ product literature retrieved from <http://eudragit.evonik.com/product/eudragit/en/products-services/eudragit-products/enteric-formulations/pages/default.aspx> on Jun. 13, 2014, p. 1.*
Takahashi, Akira et al., "Dissolution Mechanism for Hydroxypropyl Methylcellulose Acetate Succinate Used in the Enteric Coating of Tablets", *Japanese Journal of Polymer Science and Technology*, vol. 42, No. 11 (1985) pp. 803-808.
Thoma, K. et al., "Influence of aqueous coatings on the stability of enteric coated pellets and tablets", *European Journal of Pharmaceutics and Biopharmaceutics*, vol. 47, 1999, pp. 39-50.
Streubel, A. et al., "Bimodal drug release achieved with multi-layer matrix tablets: transport mechanisms and device design", *Journal of Controlled Release*, vol. 69, pp. 455-468, (2000).
R. Rowe ed, "Handbook of pharmaceutical excipients, edition 5", Jan. 2006, *Pharmaceuticla Press*, pp. 350-353.
European Search Report for European Application No. 07252398.8.

* cited by examiner

*Primary Examiner* — Suzanne Ziska
*Assistant Examiner* — Ivan Greene
(74) *Attorney, Agent, or Firm* — Alston & Bird LLP

(57) ABSTRACT

The present invention is an enteric coated granule having controlled dissolution in water even at a small coating amount; and a preparation method thereof. More specifically, provided are an enteric coated granule comprising a raw granule or a granule comprising a raw granule and at least one layer covering the raw granule, a first enteric layer covering the raw granule or the granule, and a second enteric layer formed over the first enteric layer, wherein the first and the second enteric layers comprise a first and a second hydroxypropylmethyl cellulose acetate succinates (HPMCASs) different in solubility pH, respectively, and the solubility pH value of the second HPMCAS of the second enteric layer is lower than that of the first enteric layer; and a preparation method comprising steps of covering a raw granule or a granule comprising a raw granule and at least one layer covering the raw granule with an enteric coating agent comprising a first HPMCAS to form a first enteric layer; and forming, over the first enteric layer, a second coating layer by using a second enteric coating agent comprising a second HPMCAS having a lower solubility pH value than that of the first HPMCAS.

10 Claims, No Drawings

ENTERIC COATED GRANULE AND METHOD FOR PREPARING THE SAME

BACKGROUND OF THE INVENTION

1. Field of the Invention

The present invention relates to an enteric coated granule comprising a raw granule comprising a medicinal ingredient and at least two enteric coating layers different in the solubility pH; and a method for preparing the enteric coated granule.

2. Description of the Related Art

In recent years, granules have been preferred to tablets from the biopharmacological viewpoints because there is a small individual difference in a discharge rate from the stomach and an absorption property and less influence by diet. Enteric coating is selectively employed for protecting a drug which will otherwise lose its efficacy mainly by gastric acid. It has been used widely in order to prevent and protect the gastric mucosa from the stimulation of it.

It was the common practice to employ, for enteric coating, an organic solvent type coating method comprising a step of dissolving an enteric base material in an organic solvent. Instead of this method, however, an aqueous type enteric coating method comprising a step of spraying an aqueous dispersion of enteric base material powders to form an enteric film has been preferably employed in recent years. It is from the viewpoint of safety, for example, environmental safety by preventing the release of an organic solvent to the air, safety during the preparation of granules including avoidance of fire due to an organic solvent and safety and health of personnel, and safety upon administration by eliminating the residue of an organic solvent from the final dosage form. Thus, novel enteric coated granules have been developed mainly by using the aqueous dispersion type coating.

In the aqueous dispersion type coating, a dispersion of an enteric base material in water is sprayed in the mist form to coating objects such as tablets and granules. The dispersion thus sprayed adhere uniformly to the surfaces of the coating objects, but the powders of the enteric base material dispersed in the dispersion still keep their form as are and exist discontinuously on each surface. As the dispersion which has adhered onto the surfaces of the coating objects becomes dry after spraying, a plasticizer sprayed simultaneously during coating penetrates into the particles of the enteric base material and plasticizes the enteric base material, leading to the formation of a film. The necessary coating amount varies depending on the shape of the coating objects or properties of a drug or additive to be incorporated therein such as solubility in water.

With regard to the conditions of dissolution tests relating to reevaluation of medicinal drugs, dissolution tests using various test solutions have recently been required in addition to the conventional dissolution tests in accordance with the Japanese Pharmacopoeia by using a 1st fluid (pH 1.2) and a 2nd fluid (pH 6.8). The following test solutions are listed in Iyakushin No. 599.

(a) pH 1.2: 1st fluid specified in Disintegration Test of the Japanese Pharmacopoeia.
 (b) pH 6.8: phosphate buffer solution (1→2) specified in Reagent and Test solutions of the Japanese Pharmacopoeia.
 (c) Water: purified water specified in the Japanese Pharmacopoeia.
 (d) pH 6.0: a diluted McIlvaine buffer (pH adjusted with 0.05 mol/L disodium hydrogen phosphate and 0.025 mol/L of citric acid).

Accordingly, it becomes necessary for enteric coated granules to satisfy the dissolution tests using various test solutions. This means that an enteric coated preparation has to retain acid resistance in the 1st fluid (pH 1.2) of the Japanese Pharmacopoeia and retain disintegration and dissolution properties in the 2nd fluid (pH 6.8) and moreover is required to exhibit an appropriate dissolution behavior at a pH value between these test solutions including the pH value of water. In particular, in order to retain water resistance in the dissolution test using water, the enteric coated preparation needs a large amount of coating.

An enteric coated preparation comprising a plurality of coating layers containing enteric base materials different in solubility pH is disclosed, for example, in Japanese Patent Application Unexamined Publication No. 10-203983/1998 and International Patent Application Japanese Phase Publication No. 11-506433/1999. The preparations described therein are mainly tablets having the maximum diameter of from 3 to 10 mm and are characterized in that the solubility pH of the outer enteric coating layer is higher than that of the inner enteric coating layer. An object of these preparations is to suppress the absorption of a medicinal ingredient in the small intestine and cause dissolution specifically in the colon. Accordingly, they are silent about the dissolution in water.

Enteric coated granules having at least two coating layers are described in Japanese Patent Application Unexamined Publication No. 8-109126/1996. According to the description therein, the enteric coated granules have, inside and/or outside the coating layer containing an enteric base material, a coating layer not containing an enteric base material.

In International Patent Application Japanese Phase Publication No. 2005-510539, disclosed is an enteric coated preparation comprising multiple coating layers obtained by applying protective coating on the outer surface of an enteric coating layer containing methacrylic acid-methyl methacrylate copolymer as a base material. The protective coating layer comprises a water soluble or enteric coating base material. As a specific example thereof, provided is a preparation containing two enteric coating layers wherein the inner enteric coating layer has 1:2 (molar ratio) methacrylic acid:methyl methacrylate copolymer and the outer protective coating layer has 1:1 (molar ratio) methacrylic acid:methyl methacrylate copolymer. The preparation is, however, developed not for controlling the dissolution of the granules but for physically protecting the enteric coating layer of the tablets or capsules. The 1:1 (molar ratio) methacrylic acid-methyl methacrylate copolymer contained by the protective coating layer is given as an example of a base material which is dissolved in the gastrointestinal tract earlier than the enteric coating layer so as not to disturb the drug from being released at the required site after the copolymer fulfils its purpose of protecting the enteric coating layer. Hydroxypropylmethyl cellulose acetate succinate (HPMCAS) is given as one example of the base material of such an outer layer, but its specific application is not disclosed in the publication. In addition, the above-described publication is silent about an effect on the dissolution property in water, of enteric coating layers, wherein the enteric coating layers contain HPMCASs different in the solubility pH as base materials.

SUMMARY OF THE INVENTION

With the foregoing in view, the present invention has been made. An object of the present invention is to provide an enteric coated granule having controlled dissolution into water with a small amount of coating; and a method for preparing the enteric coated granule.

The present inventors have carried out an extensive investigation in order to attain the above-described object. It has been found that an enteric coated granule having controlled dissolution into water with a small amount of coating can be prepared by applying enteric coating to a raw granule containing a medicinal ingredient, for example, using at least two kinds of HPMCASs different in the solubility pH as enteric base materials, wherein a first enteric coating layer is formed by using a coating agent containing an HPMCAS having a relatively high solubility pH and then a second enteric coating layer over the first enteric coating layer is formed by using a coating agent containing an HPMCAS having a relatively low solubility pH. Thus, the present invention has been completed.

Accordingly, the present invention provides an enteric coated granule having controlled dissolution into water with a small amount of coating amount; and a method for preparing the enteric coated granule.

According to the present invention, provided is an enteric coated granule comprising:

a raw granule or a granule comprising a raw granule and at least one layer covering the raw granule, a first enteric layer covering the raw granule or the granule, and a second enteric layer formed over the first enteric layer, wherein the first and the second enteric layers comprise a first and a second hydroxypropylmethyl cellulose acetate succinates (HPMCASs) different in solubility pH, respectively, and a solubility pH value of the second HPMCAS of the second enteric layer is lower than a solubility pH value of the first HPMCAS of the first enteric layer.

According to the present invention, provided is a method for preparing an enteric coated granule, comprising steps of:

covering a raw granule or a granule comprising a raw granule and at least one layer covering the raw granule with an enteric coating agent containing a first HPMCAS to form a first enteric layer; and forming, over the first enteric layer, a second enteric layer by using an enteric coating agent comprising a second HPMCAS having a lower solubility pH value than that of the first HPMCAS.

According to the present invention, an enteric coated granule with a small amount of coating has water resistance which cannot be generally obtained by using the conventional enteric coating technology. Hence, even when the enteric coating amount is limited, the resulting enteric coated granule has a sufficient property. In addition, even if a raw granule having a property damaged by penetration of a small amount of water is used, it can be protected from water with an appropriate amount of coating. Moreover, according to the present invention, the coating time and production cost can be reduced at the same time.

DETAILED DESCRIPTION OF THE PREFERRED EMBODIMENT(S)

The raw granule of the present invention may comprise, in addition to a medicinal ingredient, but not limited to, lactose, potato starch, crystalline cellulose, low-substituted hydroxypropyl cellulose, carmellose, hydroxypropyl cellulose, hydroxypropyl starch, carmellose calcium or the like.

The medicinal ingredient may include, but not limited to, antipyretic analgesic agents such as aspirin, lactic acid bacteria such as bifidobacteria, enzyme preparations such as pancreatin, a proton pump inhibitor such as lansoprazole, macrolide antibiotics such as erythromycin, cephem antibiotics such as cephalexin, fluorouracil prodrugs such as tegafur, expectorants such as methylcysteine hydrochloride, vitamin preparations such as pyridoxal phosphate and FAD, sodium dextransulfate and ibudilast. It should be noted that adenosine 3'-phosphate (ATP) or pharmaceutically acceptable salt thereof may sometimes be eliminated from the medicinal ingredient.

Although there is no particular limitation imposed on the average particle size of the raw granule, the raw granule having an average particle size ranging from 200 to 1,000 µm may be generally preferable. Although there is also no particular limitation imposed on the average particle size of the enteric coated granule, the average size of the enteric coated granules may be generally preferably 2 mm or less. In the preparation of the enteric coated granule according to the present invention, the advantage of the present invention can be obtained by the use of any raw granule. More specifically, an ingredient in the raw granule, that is, a medicinal ingredient or various additives in the raw granule may not be particularly limited and an amount thereof may not be particularly limited.

The granule may have an undercoat layer as a coating layer other than the first and the second enteric layers. The undercoat layer is disposed between the first enteric layer and the raw granule in order to protect the raw granule or control the dissolution property of the granule. The material of the undercoat layer may include, but not limited to, methyl cellulose, ethyl cellulose, hydroxyethyl cellulose, hydroxypropyl cellulose, hydroxypropylmethyl cellulose, polyvinyl alcohol, polyvinylpyrrolidone, cellulose acetate phthalate (CAP), hydroxypropylmethyl cellulose phthalate (HPMCP), HPMCAS, carboxymethylethyl cellulose (CMEC), methacrylic acid-ethyl acrylate copolymer, and methacrylic acid-methyl methacrylate copolymer. They may be used singly or in combination. The undercoating layer may optionally comprise a film-forming assistant such as polyethylene glycol or an adhesion inhibitor such as crystalline cellulose, lactose, calcium carbonate or talc. The coating amount of the undercoating layer may be preferably from 0.5 to 10% by weight, especially preferably from 1 to 5% by weight based on the raw granules. If necessary, a plurality of undercoating layers may be formed.

According to the present invention, HPMCASs contained in the coating agents for forming the first enteric layer and the second enteric layer each means hydroxypropylmethyl cellulose acetate succinate listed in "Japanese Pharmaceutical Excipients 1998" and it is acetic acid and succinic acid ester mixture of hydroxypropylmethyl cellulose containing from 12.0 to 28.0% by weight of a methoxyl group, from 4.0 to 23.0% by weight of a hydroxypropoxyl group, from 2.0 to 16.0% by weight of an acetyl group and from 4.0 to 28.0% by weight of a succinoyl group.

The solubility pH of HPMCAS is pH in an aqueous medium at which HPMCA starts to dissolve in the aqueous medium and a relative order of HPMCASs is defined when a test is performed using the same buffer.

Because the difference of the solubility pH of HPMCASs is utilized in the present invention, no particular limitation is imposed on the measuring method of the solubility pH insofar as it can show a relative difference in the solubility pH. Examples of the buffer employed may include McIlvaine and Clark-Lubs.

The HPMCASs different in the solubility pH may include, for example, the following A, B and C having the following substituent contents, respectively.

A: HPMCAS having from 20 to 24.0% by weight of a methoxyl group, from 5.0 to 9.0% by weight of a hydroxypropoxyl group, from 5.0 to 9.0% by weight of an acetyl group and from 14.0 to 18.0% by weight of a succinoyl group.

B: HPMCAS having from 21.0 to 25.0% by weight of a methoxyl group, from 5.0 to 9.0% by weight of a hydroxypropoxyl group, from 7.0 to 11.0% by weight of an acetyl group, and from 10.0 to 14.0% by weight of a succinoyl group.

C: HPMCAS having from 22.0 to 26.0% by weight of a methoxyl group, from 6.0 to 10.0% by weight of a hydroxypropoxyl group, from 10.0 to 14.0% by weight of an acetyl group, and from 4.0 to 8.0% by weight of a succinoyl group.

Of these, the A dissolves at the lowest pH value, the C dissolves at the highest pH value and the solubility pH of the B lies between those of A and C. According to Japanese Journal of Polymer Science and Technology, 42(11), 803-808 (November 1985), the solubility pH value of each of A, B and C as measured using a McIlvaine buffer is 5.5, 6.0 and 6.5, respectively. As the HPMCASs different in the pH solubility, mixtures of two or more of A, B and C may be used.

The total amount of the first enteric layer and second enteric layer coated may be preferably from 5 to 60% by weight, especially preferably from 10 to 30% by weight based on the raw granule.

A ratio of the amount of the first enteric layer to that of the second enteric layer (a weight ratio of the first enteric layer/the second enteric layer) in the enteric coated granule of the present invention may be preferably from (35/65) to (98/2), more preferably from (40/60) to (95/5), especially preferably from (50/50) to (95/5). Ratios outside the range of from (35/65) to (98/2) may cause deterioration in water resistance.

When the HPMCASs corresponding to A, B and C are used for the coating agents for forming the first enteric layer and the second enteric layer, combination of the HPMCASs contained by the coating agents for forming these coating layers may be preferably any one of the combination of A and B, the combination of A and C, and the combination of B and C. In particular, the combination of A and C can bring out excellent water resistance.

According to the present invention, the HPMCAS and a base material for forming other coating layer(s) may be preferably in the form of fine powders in order to attain good denseness on the surface of an object to be coated. The average particle size as measured by the laser diffraction method may be preferably less than 10 μm, especially preferably 7 μm or less. Similarly, the 90% cumulative particle size as measured by the laser diffraction method may be preferably 20 μm or less, especially preferably 15 μm or less.

Either one or both of the enteric coating agents for forming the first and the second enteric layers may preferably comprise a plasticizer.

The plasticizer may include well-known plasticizers such as triethyl citrate, triacetin, diacetin, propylene glycol, dipropylene glycol, polyethylene glycol, glycerin, glycerin fatty acid esters, sorbitan fatty acid esters, polyoxyethylene alkyl ethers, polyethylene glycol fatty acid esters and polyoxyethylene sorbitan fatty acid esters. The plasticizer may be incorporated in the HPMCAS or the base material for forming other coating layer(s). When the coating agent of the first enteric layer and that of the second enteric layer each contains a plasticizer, triethyl citrate alone or a combination of triethyl citrate and the other plasticizer or plasticizers may be especially desired.

According to the enteric coated granule of the present invention, the amount of the plasticizer to each coating agent may be preferably from 5 to 60% by weight, especially preferably from 15 to 40% by weight relative to the enteric base material (HPMCAS). When the amount of the plasticizer is less than 5% by weight, desired water resistance may not be obtained because it is difficult to plasticize the enteric base material sufficiently. When the amount is more than 60% by weight, the coated granule may form an aggregate during coating owing to the surface adhesion of the granule or coated granule may adhere to each other during storage.

According to the present invention, as a combination of HPMCAS and a plasticizer for the first enteric layer and/or the second enteric layer, the combination of HPMCAS in the form of fine powder having the above-described average particle size and triethyl citrate may be especially preferred.

When the HPMCASs different in the solubility pH are the above-described A, B and C, the amount of the plasticizer to be added to a coating agent may be preferably from 10 to 30% by weight, from 20 to 40% by weight, and from 30 to 60% by weight, especially preferably from 15 to 25% by weight, from 25 to 35% by weight, and from 30 to 40% by weight. The amount of the plasticizer to be added to the coating agent of the second enteric layer and the amount of the plasticizer to be added to the first enteric layer may be preferably not the same, though within the above-described range. The amount of the plasticizer to be added to the coating agent of the second enteric layer, that is, the coating agent containing HPMCAS having a relatively low solubility pH value may be preferably smaller. When the HPMCAS is a mixture of the above-described A, B and C, the amount of the plasticizer may be adjusted depending on the mixing ratio of A, B and C.

The above-described coating agent may comprise an adhesion preventive such as crystalline cellulose, lactose, calcium carbonate or talc, and the talc may be especially preferred. The plasticizer may be comprised because of its effect on lowering the film forming temperature of the enteric base material so that it may generate an aggregate depending on the amount of the plasticizer or the coated granule may adhere to each other during storage. In order to prevent such problems, the adhesion preventive is added.

The amount of the adhesion preventive may be preferably from 5 to 200% by weight, more preferably from 5 to 100% by weight, especially preferably from 10 to 60% by weight based on the enteric base (HPNMCAS) of each layer. When the amount is less than 5% by weight, the problems due to the adhesion such as aggregate cannot be effectively prevented. When the amount of the adhesion preventive is more than 200% by weight, it may become a cause for generating defects in the enteric coated film so that the film may not have desired acid resistance and water resistance.

In the enteric coated granule of the present invention, when either one or both of the first enteric layer and second enteric layer are formed by the aqueous dispersion type coating, the enteric coating solution to be used as a coating agent may further comprise a surfactant such as sodium lauryl sulfate, sucrose fatty acid ester, sorbitan fatty acid ester or dioctyl sodium sulfosuccinate in order to improve the wettability. Sodium lauryl sulfate may be especially preferred.

The amount of the surfactant may be preferably from 0.5 to 10% by weight, especially preferably from 1.0 to 5.0% by weight based on the enteric base material of each layer from the standpoints of dispersibility and water resistance.

An overcoat layer may be optionally formed over the enteric coating layer of the second enteric layer for the purpose of preventing mutual adhesion of the granules which have been left alone, sweetening them, or shielding their bitterness.

The overcoat layer may not be limited insofar as it is other than an enteric base material. The overcoat layer may include waxes such as stearic acid, carnauba wax and bees wax; an adhesion preventive such as lactose, calcium carbonate and talc; and coating base material such as methyl cellulose, ethyl cellulose, hydroxyethyl cellulose, hydroxypropyl cellulose, hydroxypropylmethyl cellulose, polyvinyl alcohol and polyvinylpyrrolidone. They may be used singly or in combination of two or more. When the coating base material is used, a film-forming assistant such as polyethylene glycol may be optionally added. The amount of the overcoat layer may not be particularly limited insofar as it is an amount by which a desired effect can be achieved.

A plurality of overcoating layers may be optionally formed. As overcoat layer materials, the materials same in a substance but different in a physical property depending on the amount of the substituents, may be comprised in combination.

A method for preparing the enteric coated granules of the present invention will next be described.

According to the present invention, a raw granule can be obtained by granulating a medicinal ingredient and the other ingredient or ingredients in a well-known method such as fluid bed granulation, tumbling fluidized bed granulation, agitation granulation, extrusion granulation, tumbling granulation or melt granulation. The coating solutions for forming the first enteric layer and the second enteric layer comprising HPMCASs different in the solubility pH and the other coating layer or layers may be each prepared by optionally adding a plasticizer or wettability-improving agent and dissolving the resulting mixture in an organic, or preparing an aqueous latex or an aqueous dispersion.

The aqueous dispersion type coating may be produced by dissolving a plasticizer in water, adding an additive such as surfactant to the resulting solution, and dispersing, in the solution, an enteric base material, talc and the other additive or additives dispersible in water. The produced dispersion may be used as one coating solution. Alternatively, two coating solutions may be produced as a combination of a coating solution from which only the plasticizer has been eliminated and a plasticizer solution. When the two solutions are used, they can be sprayed independently at the same time.

By using a typical coating apparatus such as a fluidized bed coating apparatus, the coating solutions prepared as described above may be applied to the raw granule successively. It may be preferred to form the coating layers not by one step but by respective steps. More specifically, a first coating agent comprising a first base material may be applied to a raw granule to form a first coating layer; a second coating agent comprising a second base material may be applied onto the first coating layer to form a second coating layer; and an optional coating layer or layers may be stacked one after another in a similar manner to form a water soluble or enteric coating layer or layers. A first enteric layer may be formed by using a coating solution comprising HPMCAS having a higher solubility pH value, and then a second enteric layer may be formed over the first enteric layer by using the coating solution comprising HPMCAS having a lower solubility pH value.

After application of the first coating agent comprising the first base material but before application of the second coating agent comprising the second base material, and/or upon completion of the application of the second coating agent comprising the second base material, a drying step of coated layer or layers can be optionally performed. Drying condition may be selected from the conditions ordinarily performed for coating of granules and may not be particularly limited insofar as the conditions do not impair the effective ingredient of the drug.

The present invention will next be described specifically by Examples and Comparative Examples. However, it should not be construed that the present invention is limited to or by the Examples.

EXAMPLE 1

(1) Preparation of Raw Granule

A granule containing 40% by weight pancreatin powder (Japan Pharmacopoeia 4×) was prepared using a centrifugal fluidizing coating granulator ("CF Coater 360S") under the below-described conditions. The granule thus obtained was sifted through a sieve of from 16-mesh to 30-mesh (opening: from 1000 to 500 μm) and provided as a raw granule used for the test.
(Granulation Conditions)
    Core granule: NP-101 (from 300 to 500 μm), charged amount: 1 kg
    Powder supplied: mixed powders of 66.7% by weight pancreatin powder and 33.3% by weight corn starch
    Binder solution: A 4% by weight HPC-L (trade name of hydroxypropyl cellulose, product of Nippon Soda) ethanol solution
    Spray air pressure: 100 kPa
    Rotation speed of rotor: 180 rpm
    Slit air flow rate: 150 L/min
    Powder supply rate: 65 g/min
    Spray rate of binder solution: 30 g/min
    Post-drying: fluidized bed drying at 60° C. for 2 hours.

(2) Preparation of Coating Solution

A necessary amount of triethyl citrate (plasticizer) was dissolved in purified water of room temperature and then a predetermined amount of sodium lauryl sulfate (wettability improver) was added thereto and dissolved. HPMCAS was added thereto and dispersed under stirring and then a predetermined amount of talc was added thereto and dispersed to produce a coating solution.

Two coating solutions were prepared for forming two coating layers. As HPMCAS contained in the coating solution for forming the first layer (first enteric layer), the HPMCAS corresponding to the above-described C ("Shin-Etsu AQOAT", product of Shin-Etsu Chemical Co., Ltd.) was used, while as HPMCAS contained in the coating solution for forming the second layer (second enteric layer), the HPMCAS corresponding to the above-described A ("Shin-Etsu AQOAT", product of Shin-Etsu Chemical Co., Ltd.) was used. The composition of each of the coating solutions is shown in Table 1.

(3) Coating Operation

The pancreatin-containing raw granule (500 g) prepared above in (1) was charged in a tumbling fluidized bed coater ("MP-01", product of Powrex Corporation) and enteric coating was performed under the below-described conditions by using the coating solutions prepared above in (2). After completion of coating of the first layer and a drying step, coating of the second layer was performed. The amount of coating of each layer is shown in Table 1.
(Coating Conditions)
    Spray system: side spray
    Filter of an exhaust system: 30# screen
    Air flow rate: 1.7 m³/min
    Spray air pressure: 150 kPa
    Spray air rate: 30 L/min
    Ejector air pressure: 200 kPa
    Intake temperature: 70° C.
    Exhaust temperature: from 36 to 40° C.
    Spray speed of coating solution: from 18 to 19 g/min
    Rotation speed of disc: 300 rpm

(4) Evaluation of Coated Granule

With regard to the enteric coated granule thus obtained finally, a protein dissolution ratio of pancreatin was measured using a dissolution tester (the paddle method of the Japanese Pharmacopoeia at 75 rpm, test solution: 900 mL) under the below-described conditions. The evaluation results are shown in Table 2.

(Measurement Conditions)
Test Solution and Time:
pH 1.2: 1st fluid specified in Disintegration Test of the Japanese Pharmacopoeia (dissolution percentage after 120 minutes).
pH 6.8: phosphate buffer solution (1→2) specified in Reagent and Test solutions of the Japanese Pharmacopoeia (dissolution percentage after 30 minutes).
Water: purified water specified under the Japanese Pharmacopoeia (dissolution percentage after 360 minutes).
Sample amount: 900 mg
Measurement: UV 265 nm

Examples 2 to 4

In a similar manner to Example 1 except that a weight ratio of the coating amount of the first layer to that of the second layer was changed as described in Table 1, an enteric coated granule was obtained and evaluated.

Comparative Example 1

In a similar manner to Example 1 except that single layer coating was performed using only the coating solution for the first layer employed in Example 1 in a coating amount greater than that of Example 1, an enteric coated granule was obtained and evaluated.

Comparative Example 2

In a similar manner to Example 1 except that single layer coating was performed using only the coating solution for the first layer employed in Example 1, an enteric coated granule was obtained and evaluated.

Comparative Example 3

In a similar manner to Example 1 except that only the coating solution for forming the second layer employed in Example 1 was used for forming the first layer, an enteric coated granule was obtained and evaluated.

Comparative Example 4

In a similar manner to Example 1 except that with regard to the composition of the coating solutions shown in Example 1, the above-described A showing dissolution at the lowest pH value among HPMCASs was contained by the coating solution for the first layer and the above-described C showing dissolution at the highest pH value among HPMCASs was contained by the coating solution for the second layer, an enteric coated granule was obtained and evaluated.

Comparative Example 5

In a similar manner to Example 1 except that with regard to the composition of the coating solutions shown in Example 1, the above-described C showing dissolution at the highest pH value among HPMCASs was contained by the coating solution for the first layer and "Eudragit L 100" (trade name; product of Röhm Pharma Co., Ltd.) was used as the coating solution for the second layer, an enteric coated granule was obtained and evaluated. "Eudragit L 100" is a 1:1 (molar ratio) methacrylic acid:methyl methacrylate copolymer having a molecular weight of 135,000 and it dissolves at pH 6 or greater.

Comparative Example 6

In a similar manner to Example 1 except that with regard to the composition of the coating solutions shown in Example 1, "Eudragit S 100" (trade name; product of Röhm Pharma Co., Ltd.) was used as the coating solution for the first layer and "Eudragit L 100" was used as the coating solution for the second layer, an enteric coated granule was obtained and evaluated. "Eudragit S 100" is a 1:2 (molar ratio) methacrylic acid:methyl methacrylate copolymer having a molecular weight of 135,000 and it dissolves at pH 7 or greater.

TABLE 1

| | | Composition of coating solution (wt %) | | | | | | | | | | | |
|---|---|---|---|---|---|---|---|---|---|---|---|---|---|
| | | first layer "a" | | | | | | | | | second layer "b" | | |
| | | HPMCAS | | Eudragit | | | | | | | HPMCAS | | Eudragit |
| | | C | A | S 100 | talc | TEC | SLS | EtOH | water | total | C | A | L 100 |
| Ex. | 1 | 7.00 | — | — | 0.70 | 2.45 | 0.21 | — | 89.64 | 100.00 | — | 7.00 | — |
| | 2 | 7.00 | — | — | 0.70 | 2.45 | 0.21 | — | 89.64 | 100.00 | — | 7.00 | — |
| | 3 | 7.00 | — | — | 0.70 | 2.45 | 0.21 | — | 89.64 | 100.00 | — | 7.00 | — |
| | 4 | 7.00 | — | — | 0.70 | 2.45 | 0.21 | — | 89.64 | 100.00 | — | 7.00 | — |
| Comp. Ex. | 1 | 7.00 | — | — | 0.70 | 2.45 | 0.21 | — | 89.64 | 100.00 | — | — | — |
| | 2 | 7.00 | — | — | 0.70 | 2.45 | 0.21 | — | 89.64 | 100.00 | — | — | — |
| | 3 | — | 7.00 | — | 0.70 | 1.40 | 0.21 | — | 90.69 | 100.00 | — | — | — |
| | 4 | — | 7.00 | — | 0.70 | 1.40 | 0.21 | — | 90.69 | 100.00 | 7.00 | — | — |
| | 5 | 7.00 | — | — | 0.70 | 2.45 | 0.21 | — | 89.64 | 100.00 | — | — | 7.00 |
| | 6 | — | — | 7.00 | 1.40 | 0.70 | — | 72.70 | 18.20 | 100.00 | — | — | 7.00 |

TABLE 1-continued

| | | Composition of coating solution (wt %) second layer "b" | | | | | amount of coating | | | |
| --- | --- | --- | --- | --- | --- | --- | --- | --- | --- | --- |
| | | | | | | | first layer a | second layer b | | |
| | | talc | TEC | SLS | EtOH | water | total | (wt %) | (wt %) | total | a/b |
| Ex. | 1 | 0.70 | 1.40 | 0.21 | — | 90.69 | 100.00 | 7.6 | 11.4 | 19.0 | 4/6 |
| | 2 | 0.70 | 1.40 | 0.21 | — | 90.69 | 100.00 | 9.5 | 9.5 | 19.0 | 5/5 |
| | 3 | 0.70 | 1.40 | 0.21 | — | 90.69 | 100.00 | 13.3 | 5.7 | 19.0 | 7/3 |
| | 4 | 0.70 | 1.40 | 0.21 | — | 90.69 | 100.00 | 18.1 | 1 | 19.1 | 95/5 |
| Comp. Ex. | 1 | — | — | — | — | — | — | 31.2 | — | 31.2 | — |
| | 2 | — | — | — | — | — | — | 19.0 | — | 19.0 | — |
| | 3 | — | — | — | — | — | — | 19.0 | — | 19.0 | — |
| | 4 | 0.70 | 2.45 | 0.21 | — | 89.64 | 100.00 | 5.7 | 13.3 | 19.0 | 3/7 |
| | 5 | 1.40 | 0.70 | — | 72.70 | 18.20 | 100.00 | 13.3 | 5.7 | 19.0 | 7/3 |
| | 6 | 1.40 | 0.70 | — | 72.70 | 18.20 | 100.00 | 13.3 | 5.7 | 19.0 | 7/3 |

* TEC repsresents triethyl citrate, SLS represents sodium laurylate, and EtOH represents ethanol.
"Amount of coating" means an weight of solid portion which is added to the raw granule.

TABLE 2

| | Dissolution (%) | | | |
| --- | --- | --- | --- | --- |
| | pH1.2 120 minutes | pH6.8 30 minutes | water 120 minutes | water 240 minutes |
| Example 1 | 3.2 | 110.0 | 7.9 | 50.7 |
| Example 2 | 1.3 | 101.8 | 4.6 | 34.4 |
| Example 3 | 1.1 | 100.9 | 0.6 | 12.8 |
| Example 4 | 3.5 | 108.2 | 4.6 | 35.8 |
| Comp. Ex. 1 | 0.9 | 96.5 | 1.5 | 8.0 |
| Comp. Ex. 2 | 2.3 | 94.5 | 21.7 | 60.5 |
| Comp. Ex. 3 | 1.3 | 101.2 | 62.0 | 84.0 |
| Comp. Ex. 4 | 2.2 | 96.6 | 8.3 | 62.7 |
| Comp. Ex. 5 | 38.3 | 110.0 | 55.7 | 81.5 |
| Comp. Ex. 6 | 20.0 | 7.2 | 17.8 | 63.1 |

As shown in Table 2, the enteric coated granules of the present invention obtained in Examples 1 to 4 have improved water resistance compared with those obtained in Comparative Examples 2 to 6 even when the coating amount is the same. In particular, the enteric coated granule obtained in Example 3 shows water resistance equivalent to one obtained in Comparative Example 1 in which the coating amount was about 1.5 times as much as that of Example 3.

A mechanism of suppressing the dissolution in water at a low coating amount in the method for preparing the enteric coated granule of the present invention will next be described referring to the above-described Examples.

The first coating solution which will be applied first to a raw granule contains the above-described C and 35% by weight triethyl citrate relative to the amount of C. The second coating solution which will be applied thereafter contains the above-described A and 20% by weight triethyl citrate relative to the amount of A. At the interface between the coating layer containing the above-described C and a larger amount of triethyl citrate and the coating layer containing the above-described A and a smaller amount of triethyl citrate, transfer of a portion of triethyl citrate may occur and the coating layer containing the above-described A as HPMCAS in the vicinity of the interface is presumed to be more dense. However, this density increase does not have an influence on the second enteric coating layer so that problems such as adhesion do not occur. By this dense interface layer, necessary and sufficient water resistance may be ensured even the coating amount is small. This result or effect can take place, as shown in Comparative Example 4, only when the solubility pH of the enteric base material in the enteric coating layer of the second enteric layer is lower than the solubility pH of the enteric base material in the coating layer adjacent thereto.

The invention claimed is:

1. An enteric coated granule comprising: a raw granule, or a granule comprising a raw granule and at least one layer covering the raw granule; a first enteric layer covering the raw granule or the granule comprising a first hydroxypropylmethyl cellulose acetate succinate (HPMCAS); and a second enteric layer formed on the first enteric layer comprising a second hydroxypropylmethyl cellulose acetate succinate (HPMCAS), wherein a solubility pH value of the second HPMCAS of the second enteric layer is lower than a solubility pH value of the first HPMCAS of the first enteric layer, wherein the total amount of the first enteric layer and the second enteric layer is 10 to 30% by weight based on the raw granule.

2. The enteric coated granule according to claim 1, wherein one or both of the first and the second enteric layers further comprise a plasticizer.

3. The enteric coated granule according to claim 2, wherein the plasticizer is triethyl citrate.

4. The enteric coated granule according to claim 1, wherein the first HPMCAS and the second HPMCAS are selected from the following groups A to C:
  A: HPMCASs having 20 to 24.0% by weight methoxyl groups, 5.0 to 9.0% by weight hydroxypropoxyl groups, 5.0 to 9.0% by weight acetyl groups and 14.0 to 18.0% by weight succinoyl groups,
  B: HPMCASs having 21.0 to 25.0% by weight methoxyl groups, 5.0 to 9.0% by weight hydroxypropoxyl groups, 7.0 to 11.0% by weight acetyl groups, and 10.0 to 14.0% by weight succinoyl groups, and
  C: HPMCASs having 22.0 to 26.0% by weight methoxyl groups, 6.0 to 10.0% by weight hydroxypropoxyl groups, 10.0 to 14.0% by weight acetyl groups, and 4.0 to 8.0% by weight succinoyl groups.

5. The enteric coated granule according to claim 1, wherein the first and the second enteric layers are formed by using an aqueous dispersion type coating solution of the HPMCAS.

6. A method for preparing an enteric coated granule, comprising steps of: covering a raw granule or a granule comprising a raw granule and at least one layer covering the raw granule with an enteric coating agent comprising a first hydroxypropylmethyl cellulose acetate succinate (HPMCAS) to form a first enteric layer; and forming, on the first enteric layer, a second enteric layer by using an enteric coating agent comprising a second HPMCAS having a lower solubility pH value than that of the first HPMCAS, wherein the total amount of the first enteric layer and the second enteric layer is 10 to 30% by weight based on the raw granule.

7. The method for preparing an enteric coated granule according to claim 6, wherein one or both of the enteric coating agents for forming the first and the second enteric layers comprise a plasticizer.

8. The method for preparing an enteric coated granule according to claim 7, wherein the plasticizer is triethyl citrate.

9. The method for preparing an enteric coated granules according to claim 6, wherein the first HPMCAS and the second HPMCAS are selected from the following groups A to C:
- A: HPMCASs having 20 to 24.0% by weight methoxyl groups, 5.0 to 9.0% by weight hydroxypropoxyl groups, 5.0 to 9.0% by weight acetyl groups and 14.0 to 18.0% by weight succinoyl groups,
- B: HPMCASs having 21.0 to 25.0% by weight methoxyl groups, 5.0 to 9.0% by weight hydroxypropoxyl groups, 7.0 to 11.0% by weight acetyl groups, and 10.0 to 14.0% by weight succinoyl groups, and
- C: HPMCASs having 22.0 to 26.0% by weight methoxyl groups, 6.0 to 10.0% by weight hydroxypropoxyl groups, 10.0 to 14.0% by weight acetyl group, and 4.0 to 8.0% by weight succinoyl group.

10. The method for preparing an enteric coated granule according to claim 6, wherein the enteric coating agents for forming the first and the second enteric layers are aqueous dispersion type coating solutions.

* * * * *